United States Patent
Kiyoto et al.

(10) Patent No.: US 8,354,426 B2
(45) Date of Patent: Jan. 15, 2013

(54) NAPHTHYRIDINE DERIVATIVE MONOHYDRATE AND METHOD FOR PRODUCING THE SAME

(75) Inventors: Taro Kiyoto, Toyama (JP); Masahiro Takebayashi, Toyama (JP); Yasutaka Baba, Toyama (JP); Muneo Syoji, Toyama (JP); Toshiya Noguchi, Tokyo (JP); Fumihito Ushiyama, Tokyo (JP); Hiroki Urabe, Tokyo (JP); Hiromasa Horikiri, Tokyo (JP)

(73) Assignees: Toyama Chemical Co., Ltd., Tokyo (JP); Taisho Pharmaceutical Co., Ltd., Tokyo (JP)

( * ) Notice: Subject to any disclaimer, the term of this patent is extended or adjusted under 35 U.S.C. 154(b) by 48 days.

(21) Appl. No.: 12/744,633

(22) PCT Filed: Nov. 25, 2008

(86) PCT No.: PCT/JP2008/071333
§ 371 (c)(1),
(2), (4) Date: May 25, 2010

(87) PCT Pub. No.: WO2009/069589
PCT Pub. Date: Jun. 4, 2009

(65) Prior Publication Data
US 2010/0249417 A1  Sep. 30, 2010

(30) Foreign Application Priority Data
Nov. 26, 2007 (JP) .................. 2007-304736

(51) Int. Cl.
*A61K 31/436* (2006.01)
*A61K 31/4353* (2006.01)
*C07D 471/04* (2006.01)
(52) U.S. Cl. ................... 514/302; 546/115
(58) Field of Classification Search .......... 514/302; 546/115
See application file for complete search history.

(56) References Cited

U.S. PATENT DOCUMENTS

| | | |
|---|---|---|
| 2006/0183749 A1 | 8/2006 | Leblond et al. |
| 2009/0036433 A1 | 2/2009 | Caileau et al. |
| 2009/0062265 A1 | 3/2009 | Jones et al. |
| 2009/0198063 A1 | 8/2009 | Kiyoto et al. |
| 2010/0152441 A1 | 6/2010 | Breault et al. |
| 2011/0092495 A1 | 4/2011 | Breault et al. |

FOREIGN PATENT DOCUMENTS

| | | |
|---|---|---|
| JP | 2006 519221 | 8/2006 |
| WO | 99 07682 | 2/1999 |
| WO | 2004 002490 | 1/2004 |
| WO | 2004 002992 | 1/2004 |
| WO | WO 2004/058144 A2 | 7/2004 |
| WO | WO 2004/058144 A3 | 7/2004 |
| WO | WO 2006/134378 A1 | 12/2006 |
| WO | WO 2007/071936 A1 | 6/2007 |
| WO | WO 2007/115947 A1 | 10/2007 |
| WO | 2007 138974 | 12/2007 |
| WO | 2008 009700 | 1/2008 |

OTHER PUBLICATIONS

Extended European Search Report issued Oct. 10, 2011 in patent application No. 08855286.4.
U.S. Appl. No. 13/468,140, filed May 10, 2012, Kiyoto, et al.
U.S. Appl. No. 13/463,434, filed May 3, 2012, Kiyoto, et al.

*Primary Examiner* — Rebecca Anderson
*Assistant Examiner* — Samantha Shterengarts
(74) *Attorney, Agent, or Firm* — Oblon, Spivak, McClelland, Maier & Neustadt, L.L.P.

(57) ABSTRACT

Disclosed is 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrate, which has strong antibacterial activity. The compound is highly safe and useful as an original drug for pharmaceutical preparations. Also disclosed is a method which is useful for producing 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrate.

3 Claims, 1 Drawing Sheet

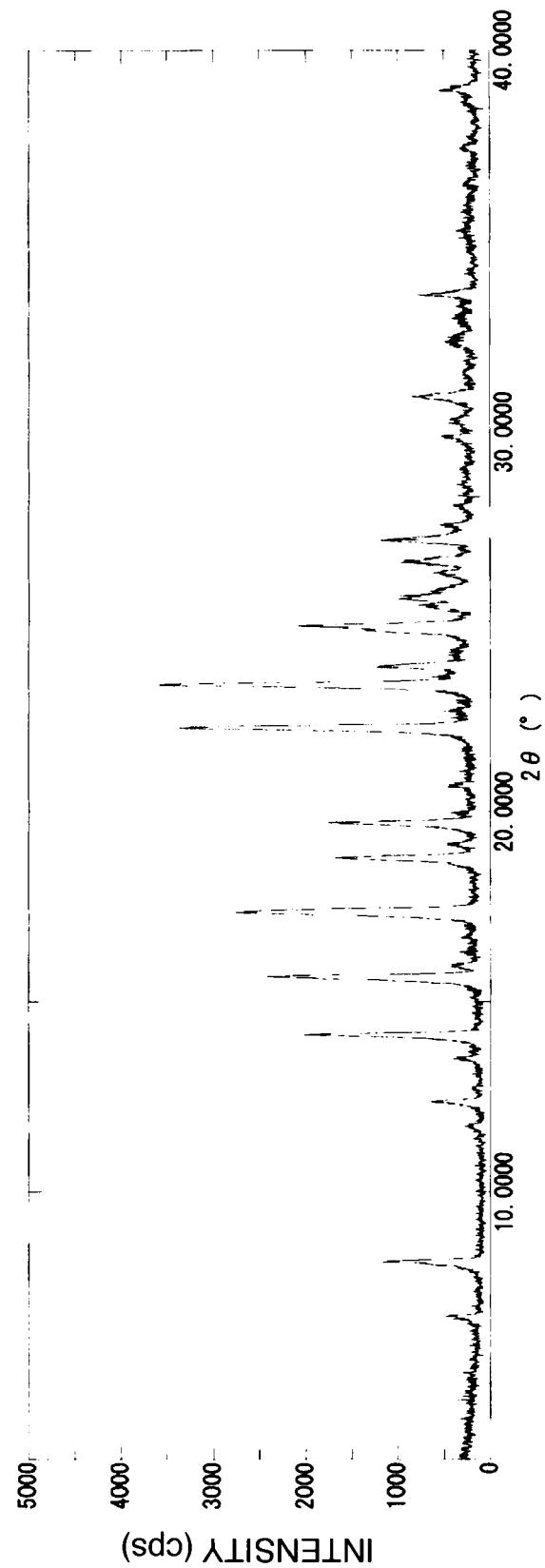

NAPHTHYRIDINE DERIVATIVE MONOHYDRATE AND METHOD FOR PRODUCING THE SAME

CROSS-REFERENCE TO RELATED APPLICATIONS

This application is a National Stage of PCT/JP08/07133 filed Nov. 25, 2008 and claims the benefit of JP 2007-304736 filed Nov. 26, 2007.

TECHNICAL FIELD

The present invention relates to a novel naphthyridine derivative monohydrate and a method for producing the same.

BACKGROUND ART

In medical practice, a wide variety of antibiotics and synthetic antibacterial agents have been used for the treatment of infectious diseases. However, resistant bacteria such as methicillin-resistant *Staphylococcus aureus* (MRSA), vancomycin-resistant *Enterococcus* (VRE) and penicillin-resistant *Streptococcus pneumoniae* (PRSP) have recently emerged. The treatment of patients infected with such a resistant organism has been a critical concern. In addition, multiresistant organisms that acquired resistance to multiple drugs have emerged. Infectious diseases caused by multiresistant organisms have been major problems worldwide as intractable diseases.

The appearance of antimicrobial agents which are effective against these resistant organisms has been strongly desired, and, for example, a quinolone compound considered to be effective against MRSA is disclosed in WO 99/07682 (PATENT DOCUMENT 1). Further, the compounds disclosed in WO 2004/002490 (PATENT DOCUMENT 2) and WO 2004/002992 (PATENT DOCUMENT 3) are known as the compounds having action mechanisms different from those of the existing drugs.

PATENT DOCUMENT 1: International Patent Publication No. WO 99/07682 pamphlet
PATENT DOCUMENT 2: International Patent Publication No. WO 2004/002490 pamphlet
PATENT DOCUMENT 3: International Patent Publication No. WO 2004/002992 pamphlet

DISCLOSURE OF THE INVENTION

Problems to be Solved by the Invention

There is a demand for the development of a drug having high safety and strong antibacterial activities against gram-positive bacteria, gram-negative bacteria and resistant bacteria. Further, a useful method for producing this drug and a useful production intermediate have been awaited with great expectations.

Means for Solving the Problems

Under such circumstances, the present inventors conducted extensive studies and found that 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrate (1) has strong antibacterial activity and high safety, (2) does not exhibit deliquescence or hygroscopicity, (3) is easy to handle, (4) is produced using a solvent which is safe to human body, (5) is produced under conditions with a little environmental burden, and (6) can be mass produced.

Further, the inventors found that 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrate can be produced easily by reacting (1) a naphthyridine derivative represented by the formula [7]

[Formula 7]

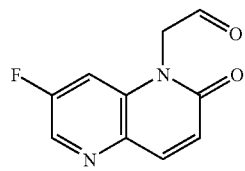

[7]

and produced by reacting a pyridine derivative represented by the formula [1]

[Formula 1]

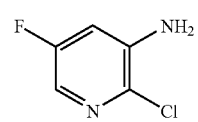

[1]

with an acrylic acid ester to give an acrylic acid derivative represented by the general formula [2]

[Formula 2]

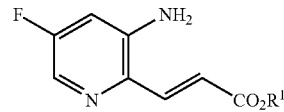

[2]

wherein $R^1$ represents an alkyl group,
then reducing/cyclizing the obtained acrylic acid derivative to give a dihydronaphthyridine derivative represented by the formula [3]

[Formula 3]

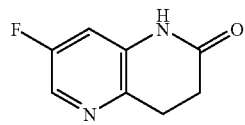

[3]

then reacting the obtained dihydronaphthyridine derivative with a compound represented by the general formula [4]

[Formula 4]

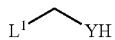

[4]

wherein $L^1$ represents a leaving group; Y represents a protected carbonyl group, to give a dihydronaphthyridine derivative represented by the general formula [5]

[Formula 5]

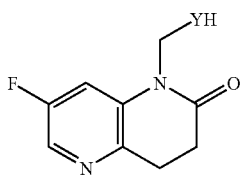

[5]

wherein Y is defined as above, then oxidizing the obtained dihydronaphthyridine derivative to give a naphthyridine derivative represented by the general formula [6]

[Formula 6]

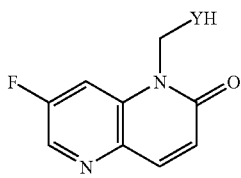

[6]

wherein Y is defined as above, and
then deprotecting the obtained naphthyridine derivative with
(2) a piperidine derivative represented by the general formula [17]

[Formula 17]

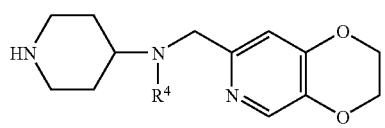

[17]

wherein $R^4$ represents an imino protecting group
and produced by reacting a kojic acid derivative represented by the general formula [8]

[Formula 8]

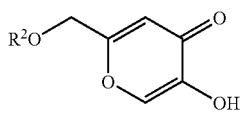

[8]

wherein $R^2$ is a hydroxyl protecting group,
with a compound represented by the general formula [9]

[Formula 9]

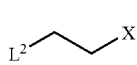

[9]

wherein $L^2$ represents a leaving group; X represents a leaving group, to give a kojic acid derivative represented by the general formula [10]

[Formula 10]

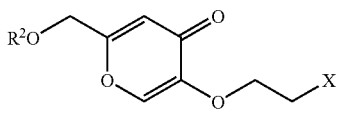

[10]

wherein $R^2$ and X are defined as above,
then deprotecting the obtained kojic acid derivative to give a kojic acid derivative represented by the general formula [11]

[Formula 11]

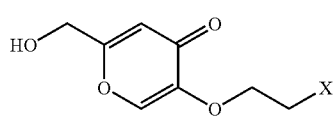

[11]

wherein X is defined as above,
then reacting the obtained kojic acid derivative with ammonia to give a pyridine derivative represented by the formula [12]

[Formula 12]

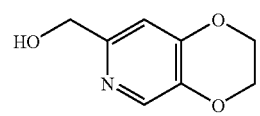

[12]

then oxidizing the obtained pyridine derivative to give a pyridine derivative represented by the formula [13]

[Formula 13]

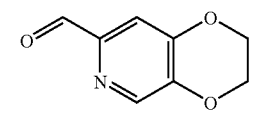

[13]

then reacting the obtained pyridine derivative with a piperidine derivative represented by the general formula [14]

[Formula 14]

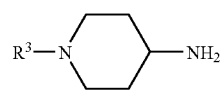

[14]

wherein $R^3$ represents an imino protecting group,
to give a piperidine derivative represented by the general formula [15]

[Formula 15]

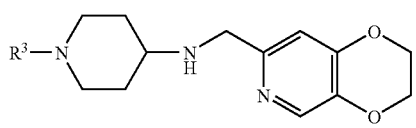

[15]

wherein $R^3$ is defined as above, then protecting the imino group to give a piperidine derivative represented by the general formula [16]

[Formula 16]

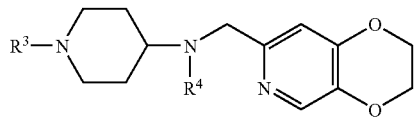

[16]

wherein $R^4$ is defined as above; $R^3$ is defined as above,
and then deprotecting the obtained piperidine derivative to give
(3) a naphthyridine derivative represented by the general formula [18]

[Formula 18]

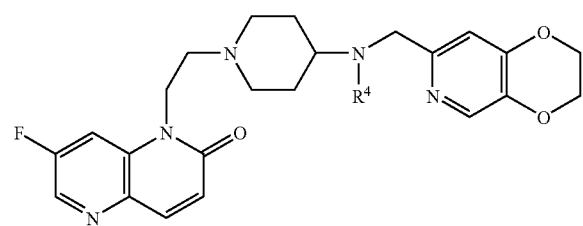

[18]

wherein $R^4$ is defined as above,
and then deprotecting the obtained naphthyridine derivative.

The inventors further found that a kojic acid derivative represented by the general formula [19]

[Formula 19]

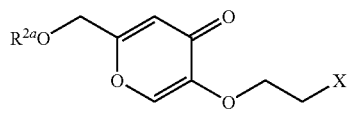

[19]

wherein $R^{2a}$ represents a hydrogen atom or a hydroxyl protecting group; X represents a leaving group
is an important production intermediate.

Advantages of the Invention 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrate of the present invention (1) has strong antibacterial activity and high safety, (2) does not exhibit deliquescence or hygroscopicity, (3) is easy to handle, (4) is produced using a solvent which is safe to human body, (5) is produced under conditions with a little environmental burden and (6) can be mass produced, and is hence useful as a bulk pharmaceutical.

The production method of the present invention has features such as (1) high yield, (2) no silica gel column chromatography required, (3) consequently little waste product and (4) no toxic or unstable reagent used, and is hence useful to produce 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrate.

Further, the kojic acid derivative represented by the general formula [19]

[Formula 20]

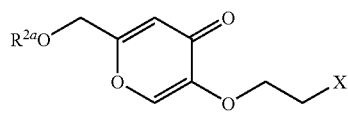

[19]

wherein $R^{2a}$ and X are defined as above
is a useful production intermediate.

BEST MODE FOR CARRYING OUT THE INVENTION

Hereinafter, the present invention will be described in detail.

In the present specification, unless otherwise specified, a halogen atom refers to, for example, a fluorine atom, a chlorine atom, a bromine atom and an iodine atom. An alkyl group refers to, for example, a straight-chain or branched-chain $C_{1-6}$ alkyl group such as methyl, ethyl, propyl, isopropyl, butyl, sec-butyl, isobutyl, tert-butyl and pentyl. An aralkyl group refers to, for example, an ar-$C_{1-6}$ alkyl group such as benzyl, diphenylmethyl, trityl, phenethyl and naphthylmethyl. An alkoxyalkyl group refers to, for example, a $C_{1-6}$ alkyloxy $C_{1-6}$ alkyl group such as methoxymethyl and 1-ethoxyethyl. An aralkyloxyalkyl group refers to, for example, an ar-$C_{1-6}$ alkyloxy $C_{1-6}$ alkyl group such as benzyloxymethyl and phenethyloxymethyl. An alkylsulfonyl group refers to, for example, a $C_{1-6}$ alkylsulfonyl group such as methylsulfonyl, trifluoromethylsulfonyl and ethylsulfonyl. An arylsulfonyl group refers to, for example, a group such as benzenesulfonyl and toluenesulfonyl. An alkylsulfonyloxy group refers to, for example, a $C_{1-6}$ alkylsulfonyloxy group such as methylsulfonyloxy, trifluoromethylsulfonyloxy and ethylsulfonyloxy. An arylsulfonyloxy group refers to, for example, a group such as benzenesulfonyloxy and toluenesulfonyloxy.

An acyl group refers to, for example, a formyl group, a straight-chain or branched-chain $C_{2-6}$ alkanoyl group such as acetyl, propionyl, butyryl, isovaleryl and pivaloyl, an ar $C_{1-6}$ alkylcarbonyl group such as benzylcarbonyl, a cyclic hydrocarbon carbonyl group such as benzoyl and naphthoyl, and a heterocyclic carbonyl group such as nicotinoyl, thenoyl, pyrrolizinocarbonyl and furoyl. An alkoxycarbonyl group refers to, for example, a straight-chain or branched-chain $C_{1-6}$ alkyloxycarbonyl group such as methoxycarbonyl, ethoxycarbonyl, 1,1-dimethylpropoxycarbonyl, isopropoxycarbonyl, 2-ethylhexyloxycarbonyl, tert-butoxycarbonyl and tert-pentyloxycarbonyl. An aralkyloxycarbonyl group refers to, for example, an ar $C_{1-6}$ alkyloxycarbonyl group such as benzyloxycarbonyl and phenethyloxycarbonyl.

An oxygen-containing heterocyclic group refers to, for example, a group such as tetrahydropyranyl and tetrahydrofuranyl. A sulfur-containing heterocyclic group refers to, for example, a group such as tetrahydrothiopyranyl. A protected carbonyl group refers to, for example, a group formed from a carbonyl group and an alcohol, such as (hydroxy)(methoxy)methylene, (hydroxy)(ethoxy)methylene, (hydroxy)(propoxy)methylene, (hydroxy)(isopropoxy)methylene, (hydroxy)(butoxy)methylene, (hydroxy)(pentyloxy)methylene, (hydroxy)(hexyloxy)methylene, (hydroxy)(heptyloxy)methylene, (hydroxy)(octyloxy)methylene, (hydroxy)(1,1-dimethylpropoxy)methylene, dimethoxymethylene, diethoxymethylene, dipropoxymethylene, diisopropoxymethylene, dibutoxymethylene, bis(benzyloxy)methylene, 1,3-dioxolan-2-ylidene and 1,3-dioxan-2-ylidene, a group formed from a carbonyl group and a thiol, such as bis(methylthio)methylene, bis(ethylthio)methylene, bis(benzylthio)methylene, 1,3-dithiolan-2-ylidene and 1,3-dithian-2-ylidene, and a group such as oxazolin-2-ylidene, imidazolidin-2-ylidene and thiazolidin-2-ylidene. A leaving group refers to, for example, a halogen atom, an alkylsulfonyloxy group and an arylsulfonyloxy group.

A hydroxyl protecting group encompasses all groups which are usable as a usual hydroxyl protecting group, and examples include groups described in "Greene's Protective Groups in Organic Synthesis" by M. Wuts and W. Greene, 4th edition, John Wiley & Sons, INC., 2006, p. 16 to 366. Specific examples include an acyl group, an alkoxycarbonyl group, an aralkyloxycarbonyl group, an alkyl group, an aralkyl group, an oxygen-containing heterocyclic group, a sulfur-containing heterocyclic group, an alkoxyalkyl group, an aralkyloxyalkyl group, an alkylsulfonyl group, and an arylsulfonyl group.

An imino protecting group encompasses all groups which are usable as a usual imino protecting group, and examples include groups described in "Greene's Protective Groups in Organic Synthesis" by M. Wuts and W. Greene, 4th edition, John Wiley & Sons, INC., 2006, p. 696 to 926. Specific examples include an acyl group, an alkoxycarbonyl group, an aralkyloxycarbonyl group, an aralkyl group, an alkylsulfonyl group, and an arylsulfonyl group.

Preferable 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrates used in the present invention are the following compounds.

The crystals of the 1-(2-(4-((2,3-dihydro(1,4)dioxino(2,3-c)pyridin-7-ylmethyl)amino)piperidin-1-yl)ethyl-7-fluoro-1,5-naphthyridin-2(1H)-one monohydrate having the diffraction angles 2θ of 6.8°, 8.2°, 14.2° and 15.7° in the powder X-ray diffraction pattern are preferable.

In addition, characteristic peaks of powder X-ray diffraction may vary depending on measurement conditions. For this reason, the peak in the powder x-ray diffraction of the compound of the present invention should not be strictly interpreted.

In the present invention, preferable production methods include the following methods.

The production method wherein $R^1$ is an ethyl group, a propyl group or a butyl group is preferable, with the production method wherein $R^1$ is a butyl group being more preferable.

The production method wherein $R^2$ is an acyl group, an aralkyl group or an oxygen-containing heterocyclic group is preferable, with the production method wherein $R^2$ is an oxygen-containing heterocyclic group being more preferable, and with the production method wherein $R^2$ is a tetrahydropyranyl group being further preferable.

The production method wherein $R^3$ is an acyl group, an alkoxycarbonyl group or an aralkyl group is preferable, with the production method wherein $R^3$ is an aralkyl group being more preferable, and with the production method wherein $R^3$ is a benzyl group being further preferable.

The production method wherein $R^4$ is an acyl group, an alkoxycarbonyl group or an aralkyl group is preferable, with the production method wherein $R^4$ is an acyl group or an alkoxycarbonyl group being more preferable, and with the production method wherein $R^4$ is an alkoxycarbonyl group being further preferable.

The production method wherein X is a chloride atom is preferable.

The production method wherein Y is a dimethoxymethylene group, a diethoxymethylene group, a dipropoxymethylene group, a 1,3-dioxolan-2-ylidene group or a 1,3-dioxan-2-ylidene group is preferable, with the production method wherein Y is a dimethoxymethylene group, a diethoxymethylene group or a 1,3-dioxolan-2-ylidene group being more preferable, and with the production method wherein Y is a dimethoxymethylene group being further preferable.

In the compound represented by the general formula [19], preferable compounds include the following compounds.

The compound wherein $R^{2a}$ is a hydrogen atom, an acyl group, an aralkyl group or an oxygen-containing heterocyclic group is preferable, with the compound wherein $R^{2a}$ is a hydrogen atom or an oxygen-containing heterocyclic group being more preferable, with the compound wherein $R^{2a}$ is a hydrogen atom or a tetrahydropyranyl group being further preferable, and with the compound wherein $R^{2a}$ is a hydrogen atom being the most preferable.

The production method of the present invention is hereinafter described.

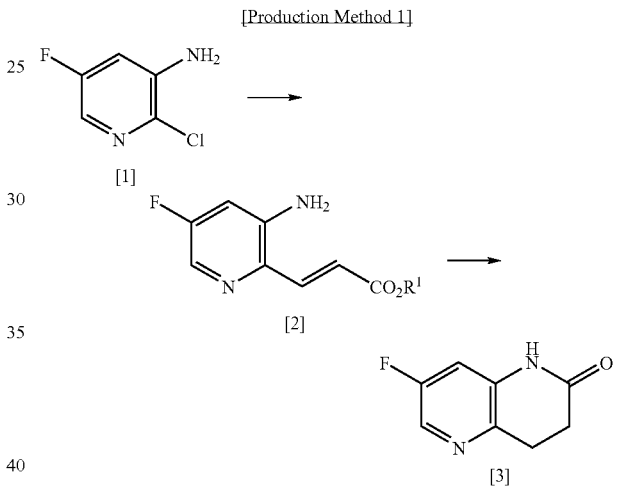

[Production Method 1]

wherein $R^1$ is defined as above.

(1-1)

The compound of the general formula [2] can be produced by reacting the compound of the formula [1] with an acrylic acid ester in the presence of a catalyst, in the presence or absence of a base, and in the presence or absence of a ligand. The reaction may be carried out, for example, by the method described in "Chem. Rev." by I. P. Beletskaya and A. V. Cheprakov, 2000, Vol. 100, p. 3009 to 3066, or by any method in accordance therewith.

(1-2)

The compound of the formula [3] can be produced by reducing/cyclizing the compound of the general formula [2] in the presence of a catalyst.

The reduction reaction may be carried out, for example, by the method described in "Comprehensive Organic Transformations" by Richard C. Larock, VCH Publishers, INC., 1989, p. 6 to 17, or any method in accordance therewith.

The solvent used in the reduction reaction may be any solvent insofar as it does not affect the reaction, and examples include alcohols such as methanol, ethanol, 2-propanol and 2-methyl-2-propanol; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether, dibutyl ether and ethylene glycol monomethyl ether; sulfoxides such as dimethyl sulfoxide, esters such as ethyl acetate and butyl acetate; amides such as N,N-dimethylformamide, N,N-dimethylacetamide and 1-methyl-2-pyrrolidone; ketones such as acetone and 2-butanone as well as water, and these solvents may be used in mixture. Preferable examples of the solvent are methanol and ethanol.

The catalyst used in the reduction reaction includes, for example, palladium carbon, palladium acetate, platinum oxide, rhodium carbon and ruthenium chloride. A preferable catalyst is palladium carbon.

The reducing agent used in the reduction reaction includes, for example, hydrogen; formic acid; formates such as sodium formate, ammonium formate and formic acid triethylammonium; and cyclohexene. Preferable reducing agents include hydrogen and formic acid.

The amount of the catalyst used may be 0.001 to 5 times weight, preferably 0.01 to 0.5 times weight, with respect to the compound of the general formula [2].

The amount of the reducing agent may be 1 to 100 times by mole, preferably 1 to 5 times by mole, with respect to the compound of the general formula [2].

The reduction reaction may be carried out at −30 to 150° C., preferably 0 to 100° C., for 30 minutes to 120 hours.

The solvent used in the cyclization reaction may be any solvent insofar as it does not affect the reaction, and examples include alcohols such as methanol, ethanol, 2-propanol and 2-methyl-2-propanol; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether, dibutyl ether and ethylene glycol monomethyl ether; sulfoxides such as dimethyl sulfoxide; esters such as ethyl acetate and butyl acetate; amides such as N,N-dimethylformamide, N,N-dimethylacetamide and 1-methyl-2-pyrrolidone; ketones such as acetone and 2-butanone as well as water, and these solvents may be used in mixture. Preferable solvents include toluene and xylene.

The cyclization reaction may be carried out at 0 to 200° C., preferably 50 to 130° C., for 30 minutes to 120 hours.

(1-3)

The compound of the formula [3] can be produced by reacting the compound of the formula [1] with an acrylic acid ester in the presence of a catalyst, in the presence or absence of a base, in the presence or absence of a ligand; and in the presence of a reducing agent. The reaction is a one-pot reaction to produce the compound of the formula [3]. The reaction may be carried out in accordance with the production method (1-1) and the production method (1-2).

[Production Method 2]

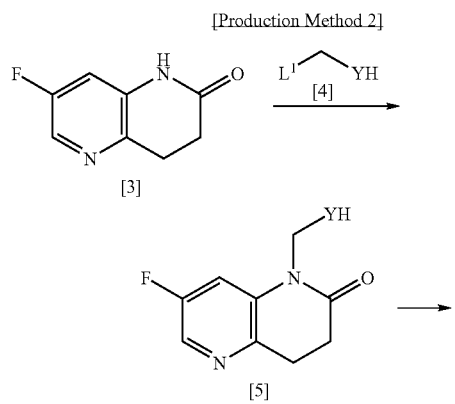

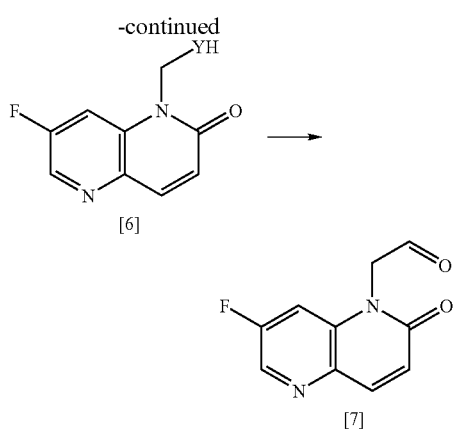

wherein $L^1$ and Y are defined as above.

(2-1)

Known compounds of the general formula [4] are, for example, 2-(2-bromomethyl)-1,3-dioxolane, 2-bromo-1,1-diethoxyethane and 2-bromo-1,1-dimethoxyethane.

The compound of the general formula [5] can be produced by reacting the compound of the general formula [4] with the compound of the formula [3] in the presence of a base.

The solvent used in this reaction may be any solvent insofar as it does not affect the reaction, and examples include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether, sulfoxides such dimethyl sulfoxide; esters such as ethyl acetate as well as water, and these solvents may be used in mixture. Preferable solvents are N,N-dimethylacetamide and dimethyl sulfoxide.

The base used in this reaction includes, for example, organic bases such as pyridine, dimethylaminopyridine, triethylamine, sodium tert-butoxide and potassium tert-butoxide as well as inorganic bases such as sodium hydride, sodium hydroxide, potassium hydroxide, sodium hydrogen carbonate, sodium carbonate, potassium carbonate, potassium phosphate and cesium carbonate. Preferable bases are potassium carbonate and potassium phosphate.

The amounts of the base and the general formula [4] compound used may be 1 to 50 times by mole, preferably 1 to 5 times by mole, with respect to the compound of the formula [3].

The reaction may be carried out at −30 to 150° C., preferably 0 to 100° C., for 30 minutes to 48 hours.

(2-2)

The compound of the general formula [6] can be produced by oxidizing the compound of the general formula [5] in the presence or absence of a radical initiator, in the presence or absence of a base. The reaction may be carried out, for example, by the methods described in Chem. Rev., by Djerassi C., p. 271 to 317, Vol. 43, 1948 and "Bioorg. Med. Chem. Lett.", by Julianne A. Hunt, 2003, Vol. 13, p. 467 to 470, or by any method in accordance therewith.

The solvent used in this reaction may be any solvent insofar as it does not affect the reaction, and examples include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene and chlorobenzene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethyl sulfoxide as well as esters such as ethyl acetate, and these solvents may be used in mixture. A preferable solvent is chlorobenzene.

The oxidizing agent used in this reaction includes, for example, bromide, chlorine, iodine, N-bromosuccinimide, N-chlorosuccinimide, N-iodosuccinimide and manganese dioxide.

A preferable oxidizing agent is N-bromosuccinimide.

The radical initiator used as necessary in this reaction includes, for example, azobisisobutyronitrile, benzoyl peroxide and 2,2'-azobis(4-methoxy-2,4-dimethylvaleronitrile).

A preferable radical initiator is 2,4'-azobis(4-methoxy-2,4-dimethylvaleronitrile).

The base used as necessary in this reaction includes, for example, organic bases such as pyridine, dimethylamino pyridine, triethylamine, sodium tert-butoxide and potassium tert-butoxide as well as inorganic bases such as sodium hydride, sodium hydroxide, potassium hydroxide, sodium bicarbonate, sodium carbonate, potassium carbonate, barium carbonate and cesium carbonate. A preferable base is potassium carbonate.

The amount of the oxidizing agent used is 1 to 30 times by mole, preferably 1 to 5 times by mole, with respect to the compound of the formula [5].

The amount of the radical initiator used as necessary is 0.0001 to 0.5 times by mole, preferably 0.001 to 0.1 times by mole, with respect to the compound of the formula [5].

The reaction may be carried out at −30 to 150° C., preferably 0 to 100° C., for 30 minutes to 48 hours.

The compound of the general formula [6] is, for example, 1-(2,2-diethoxyethyl)-7-fluoro-1,5-naphthyridin-2(1H)-one. 1-(2,2-Diethoxyethyl)-7-fluoro-1,5-naphthyridin-2(1H)-one can be produced by reacting 7-fluoro-1,5-naphthyridin-2 (1H)-one with 2-bromo-1,1-diethoxyethane.

The reaction may be carried out by the method described in WO 2007/138974 or by any method in accordance therewith.

(2-3)

The compound of the formula [7] can be produced by deprotecting the compound of the general formula [6]. The reaction may be carried out, for example, by the method described in "Greene's Protective Groups in Organic Synthesis" by M. Wuts and W. Greene, 4th edition, John Wiley & Sons, INC., 2006, p. 435 to 505 or by any method in accordance therewith.

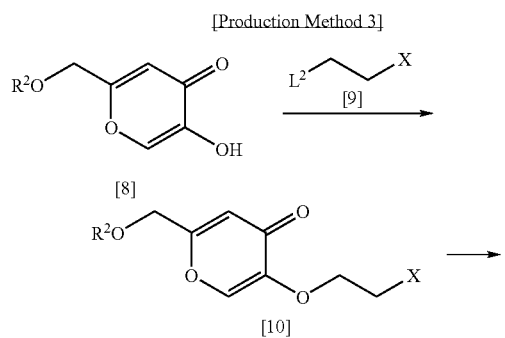

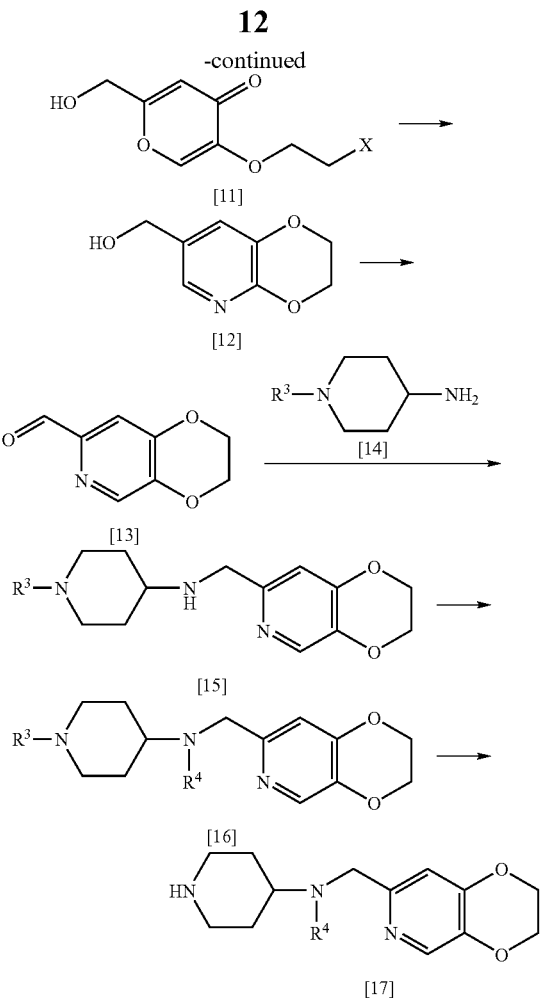

wherein $R^2$, $R^3$, $R^4$, $L^2$ and X are defined as above.

The compound of the general formula [8] can be produced from kojic acid.

(3-1)

Known compounds of the general formula [9] include, for example, 1-bromo-2-chloroethane and 1,2-dibromoethane.

The compound of the general formula [10] can be produced by reacting the compound of the general formula [9] with the compound of the general formula [8] in the presence of a base.

The reaction may be carried out in accordance with Production Method 2-1.

(3-2)

The compound of the general formula [11] can be produced by deprotecting the compound of the general formula [10]. The reaction may be carried out, for example, by the method described in "Greene's Protective Groups in Organic Synthesis" by M. Wuts and W. Greene, 4th edition, John Wiley & Sons, INC., 2006, p. 16 to 366 or by any method in accordance therewith.

Further, the compound of the general formula [11] can be produced by reacting the compound of the general formula [9] with kojic acid. The reaction may be carried out in accordance with Production Method 3-1.

(3-3)

The compound of the formula [12] can be produced by reacting the compound of the general formula [11] with ammonia.

The solvent used in this reaction may be any solvent insofar as it does not affect the reaction, and examples include alcohols such as methanol, ethanol, 2-propanol and 2-methyl-2-propanol; aromatic hydrocarbons such as benzene, toluene, and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethyl sulfoxide; esters such as ethyl acetate; amides such as N,N-dimethylformamide, N,N-dimethylacetamide and 1-methyl-2-pyrrolidone as well as water, and these solvents may be used in mixture. A preferable solvent includes water.

The ammonia used in this reaction includes ammonia water and so on. The amount of the ammonia used may be 1 to 100 times by mole, preferably 1 to 30 times by mole, with respect to the compound of the general formula [11].

The reaction may be carried out at room temperature to 150° C., preferably 50 to 100° C., for 30 minutes to 120 hours.
(3-4)

The compound of the formula [13] can be produced by oxidizing the compound of the formula [12]. The reaction may be carried out by the methods described in "Advanced Organic Chemistry", by Jerry March, the 4th edition, John Wiley & Sons, INC., 1992, p. 1167 to 1171 and "Comprehensive Organic Transformations" by Richard C. Larock, VCH Publishers, INC., 1989, p. 604 to 614 or any method in accordance therewith.

The solvent used in the reaction may be any solvent insofar as it does not affect the reaction, and examples include halogenated hydrocarbons such as methylene chloride, chloroform and dichloroethane; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethyl sulfoxide; esters such as ethyl acetate; amides such as N,N-dimethylformamide, N,N-dimethylacetamide and 1-methyl-2-pyrrolidone; acids such as acetic acid as well as water, and these solvents may be used in mixture. A preferable solvent includes tetrahydrofuran.

The oxidizing agent used in this reaction includes, for example, dimethyl sulfoxide, chromium trioxide, manganese dioxide and chromyl chloride. A preferable oxidizing agent includes manganese dioxide.

The amount of the oxidizing agent used in the reaction is 1 to 30 times by mole, preferably 1 to 5 times by mole, with respect to the compound of the formula [12].

The reaction may be carried out at −78 to 200° C., preferably 0 to 100° C., for 30 minutes to 48 hours.
(3-5)

The compound of the general formula [15] can be produced by reacting the compound of the general formula [14] with the compound of the formula [13] in the presence of a reducing agent. The reaction may be carried out by the methods described in WO 02/50061, WO 02/56882, "Advanced Organic Chemistry", by Jerry March, the 4th edition, John Wiley & Sons, INC., 1992, p. 898 to 900 and "Comprehensive Organic Transformations" by Richard C. Larock, VCH Publishers, INC., 1989, p. 421 to 425 or any method in accordance therewith.

The solvent used in the reaction may be any solvent insofar as it does not affect the reaction, and examples include alcohols such as methanol, ethanol, 2-propanol and 2-methyl-2-propanol; halogenated hydrocarbons such as methylene chloride, chloroform and dichloroethane; aromatic hydrocarbons such as benzene, toluene, and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethyl sulfoxide; esters such as ethyl acetate; amides such as N,N-dimethylformamide, N,N-dimethylacetamide and 1-methyl-2-pyrrolidone as well as water, and these solvents may be used in mixture. A preferable solvent includes methanol.

The reducing agent used in this reaction includes, for example, hydride complexes such as lithium aluminum hydride, sodium triacetoxyborohydride, sodium cyanoborohydride and sodium borohydride, borane, sodium as well as sodium amalgam. Alternatively, electrolytic reduction which uses copper or platinum for the cathode; catalytic reduction which uses Raney nickel, platinum oxide or palladium black as well as the reduction which uses "zinc/acid" may also be used. A preferable reducing agent includes sodium borohydride. Sodium borohydride can be used in the form of solid or solution.

The amounts of the compound of the general formula [14] and the reducing agent used in the reaction are 1 to 50 times by mole, preferably 1 to 5 times by mole, with respect to the compound of the formula [13].

The reaction may be carried out at −30 to 150° C., preferably 0 to 100° C., for 10 minutes to 120 hours.
(3-6)

The compound of the general formula [16] can be produced by protecting the imino group of the compound of the general formula [15]. The reaction may be carried out, for example, by the method described in "Greene's Protective Groups in Organic Synthesis" by M. Wuts and W. Greene, 4th edition, John Wiley & Sons, INC., 2006, p. 696 to 926 or any method in accordance therewith.
(3-7)

The compound of the general formula [17] can be produced by deprotecting the compound of the general formula [16]. The reaction may be carried out, for example, by the method described in "Greene's Protective Groups in Organic Synthesis" by M. Wuts and W. Greene, 4th edition, John Wiley & Sons, INC., 2006, p. 696 to 926 or any method in accordance therewith.

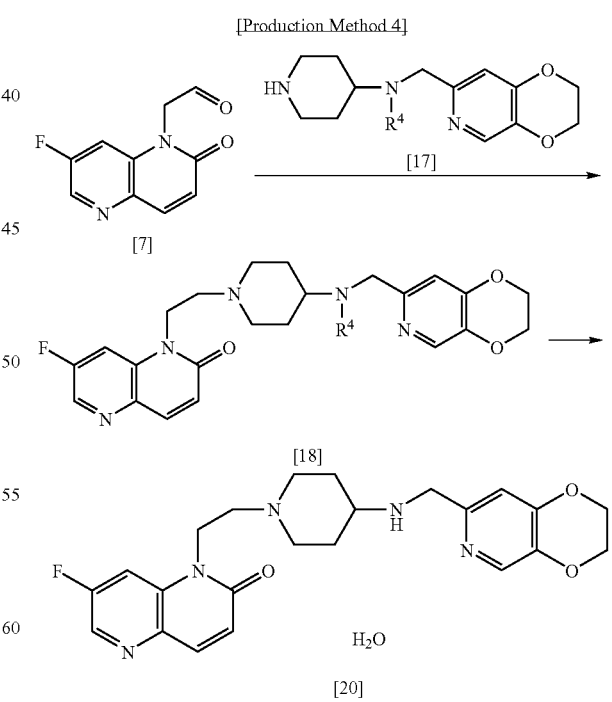

wherein R⁴ is defined as above.
(4-1)

The compound of the general formula [18] can be produced by reacting the compound of the general formula [17]

with the compound of the formula [7]. The reaction may be carried out in accordance with Production Method 3-5.

(4-2)

The compound of the formula [20] can be produced by deprotecting the compound of the general formula [18], followed by neutralization crystallization. The deprotection reaction may be carried out, for example, by the method described in "Greene's Protective Groups in Organic Synthesis" by M. Wuts and W. Greene, 4th edition, John Wiley & Sons, INC., 2006, p. 696 to 926 or any method in accordance therewith.

The solvent used in this reaction may be any solvent insofar as it does not adversely affect the reaction, and examples include mixed solvents of water and organic solvents as well as water.

The organic solvent includes, for example, alcohols such as methanol, ethanol, 2-propanol and 2-methyl-2-propanol; halogenated hydrocarbons such as methylene chloride, chloroform and dichloroethane; aromatic hydrocarbons such as benzene, toluene, and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as a dimethyl sulfoxide, esters such as ethyl acetate; ketones such as acetone and 2-butanone; amides such as N,N-dimethylformamide, N,N-dimethylacetamide and 1-methyl-2-pyrrolidone; and these solvents may be used in mixture.

Preferable solvents include mixed solvents of water and alcohols as well as water, with water being more preferable.

When mixed solvents of water and an organic solvent(s) are used, the ratio of water to an organic solvent(s) (water/organic solvent) is within the range of preferably 100/0 to 50/50, more preferably 100/0 to 80/10.

The reaction may be carried out at −20 to 120° C., preferably 10 to 80° C., for 10 minutes to 120 hours.

The production method of the present invention has features such as (1) high yield, (2) no silica gel column chromatography required, (3) consequently little waste is produced and (4) no toxic or unstable reagent used, and is hence useful as an industrial production method.

In Production Methods 1 to 4, the compounds of the formulae [3], [7], [12] and as well as the compounds of the general formulae [2], [5], [6], [8], [10], [11], [15], [16], [17] and [18] can be isolated and purified, but may be used for the following reaction without being isolated.

When the compound of the present invention represented by the formula [20] is used as a pharmaceutical product, pharmaceutical adjuncts routinely used for the drug formulation such as an excipient, a carrier and a diluent may be mixed as necessary. These can be administered orally or parenterally in accordance with a routine manner in the dosage form of tablets, capsules, powders, syrups, granules, pills, suspensions, emulsions, liquids/solutions, particulate preparations, suppositories, ophthalmic solutions, nasal drops, ear drops, patches, ointments or injections. The route, dosage and frequency of the administration can be suitably selected according to the age, weight and symptoms of a patient. The compound as a pharmaceutical product may typically be administered orally or parenterally (e.g., administration by injection, intravenous drip or to a rectum site) in a dose of 0.01 to 1000 mg/kg to an adult at one to several times a day.

The compound of the present invention represented by the formula [20] exhibits good antibacterial activities against gram-positive bacteria including resistant bacteria such as multiresistant *Staphylococcus aureus*, multiresistant pneumococci and vancomycin-resistant *Enterococcus*, gram-negative bacteria, anaerobe or atypical mycobacteria.

More specifically, the compound of the present invention exhibits good antibacterial activities against organisms selected from *Staphylococcus aureus* (*Staphylococcus aureus* Smith, *Staphylococcus aureus* FDA 209P, *Staphylococcus aureus* F-3095 (multiresistant *Staphylococcus aureus*)), *Staphylococcus aureus* F-2161 (multiresistant *Staphylococcus aureus*), *Streptococcus pneumococci* (*Streptococcus pneumoniae* IID553, *Streptococcus pneumoniae* D-1687 (QRSP), *Streptococcus pneumoniae* D-4249 (MDRSP)), *Enterococcus faecalis* (*Enterococcus faecalis* ATCC29212, *Enterococcus faecalis* IID682, *Enterococcus faecalis* D-2648 (VCM-R), *Enterococcus faecalis* EF-210 (VanA type VRE), *Enterococcus faecium* (*Enterococcus faecium* NBRC 13712, *Enterococcus faecium* EF-211 (VanA type VRE)), *Corynebacterium diphtheriae* (*Corynebacterium diphtheriae* ATCC 27010), *Escherichia coli* (*Escherichia coli* NIHJ), *Serratia marcescens* (*Serratia marcescens* IID5218), *Haemophilus influenzae* (*Haemophilus influenzae* ATCC 49247), *Moraxella catarrhalis* (*Moraxella catarrhalis* ATCC 25238), *Pseudomonas aeruginosa* (*Pseudomonas aeruginosa* IFO3445), *Enterobacter cloacae* (*Enterobacter cloacae* IID 977), *Citrobacter freundii* (*Citrobacter freundii* NBRC 12681), *Gardnerella vaginalis* (*Gardnerella vaginalis* ATCC 14018), *Neisseria gonorrhoeae* (*Neisseria gonorrhoeae* ATCC 19424), *Peptostreptococcus asaccharolyticus* (*Peptostreptococcus asaccharolyticus* ATCC 14963), *Propionibacterium acnes* (*Propionibacterium acnes* JCM 6425), *Clostridium perfringens* (*Clostridium perfringens* ATCC 13124), *Bacteroides fragilis* (*Bacteroides fragilis* ATCC 25285), *Porphyromonas gingivalis* (*Porphyromonas gingivalis* JCM 8525), *Prevotella intermedia* (*Prevotella intermedia* JCM 7365), *Fusobacterium nucleatum* (*Fusobacterium nucleatum* JCM 8532), *Legionella pneumophilia* (*Legionella pneumophilia* ATCC33153, *Legionella pneumophilia* subsp. *pneumophilia* ATCC33155, *Legionella pneumophilia* subsp. *pneumophilia* ATCC33215, *Legionella pneumophilia* subsp. *fraseri* ATCC33216) and *Mycoplasma pneumoniae* (*Mycoplasma pneumoniae* ATCC15531)

The compound of the present invention represented by the formula [20] exhibits good safety. The safety is evaluated by a wide variety of tests, which are selected from various safety tests including, for example, a cytotoxicity test, a selectivity test targeting to DNA gyrase in human and organisms, a selectivity test targeting to topoisomerase IV in human and organisms, hERG test, repeated-dose toxicity study, cytochrome P450 (CYP) activity inhibition test, metabolism dependent inhibition test, in vivo mouse micronucleus assay and in vivo rat liver USD assay.

The compound of the present invention represented by the formula [20] has good metabolic stability. The metabolic stability is evaluated by a wide variety of tests, which are selected from various stability tests including, for example, human liver microsome metabolic stability assay and human S9 metabolic stability assay.

Hereinafter, the usefulness of the compound of the present invention represented by the formula [20] is described with reference to the following Test Examples.

TEST EXAMPLE 1

Susceptibility Test

The compound of Example 16 was selected as the compound of the present invention.

The compound of the present invention was dissolved in dimethyl sulfoxide and measured for the antibacterial activity (MIC) by a microtiter broth dilution method recommended by Japanese Society of Chemotherapy.

*Staphylococcus aureus* (*S. aureus* Smith, FDA209P, F-3095), *Enterococcus faecalis* (*E. faecalis* D-2648) and *Escherichia coli* (*E. coli* NIHJ) were used as the bacteria.

The bacterial cells, grown overnight on a Mueller-Hinton agar: MHA plate at 35° C., were suspended in a sterilized physiological saline so as to be a 0.5 McFarland equivalent standard. The cell suspension was diluted ten-fold to prepare an inoculum. Approximately 0.005 mL of the inoculum was inoculated into a cation-adjusted Mueller-Hinton broth (CAMHB), 100 μL/well containing the test substance and allowed to grow overnight at 35° C. The lowest concentration of the test substance at which no bacterial growth was observed by the naked eye was determined as MIC.

Table 1 shows the results.

TABLE 1

|  | MIC(μg/mL) |
| --- | --- |
| *S. aureus* Smith | 0.0625 |
| *S. aureus* FDA209P | 0.0313 |
| *S. aureus* F-3095 | 0.0313 |
| *E. faecalis* D-2648 | 0.25 |
| *E. coli* NIHJ | 0.125 |

The compound of the present invention demonstrated good antibacterial activities against various bacterial strains.

TEST EXAMPLE 2

Hygroscopicity Test

The compound of Example 16 was selected as the compound of the present invention. The compound of Comparative Example 1 was selected as the comparative compound.

The compound of the present invention and the comparative compound were stored for three weeks under the conditions of room temperature and the relative humidity of 97%. As a result, the compound of the present invention was powder with no apparent change. On the other hand, the comparative compound had deliquesced.

The compound of the present invention exhibited high stability.

TEST EXAMPLE 3

Solubility

The compound of Example 16 was selected as the compound of the present invention.

The compound of the present invention was added in an excessive amount to a 0.2 mol/L phosphate buffer solution (pH 6.5), and the mixture was shaken for 48 hours in a thermostatic shaker (25° C.), and centrifuged, and the supernatant thereof was filtered through a filter having a pore size of 0.45 μm, whereby the solubility was measured by high speed liquid chromatography. As a result, the solubility to the 0.2 mol/L phosphate buffer solution (pH 6.5) was 21.2 mg/mL.

EXAMPLE

The present invention is described in reference to the following examples, but is not limited thereto.

Each abbreviated symbol means as follows.

Boc:tert-butoxycarbonyl, Bn:benzyl, Bu:butyl, Me:methyl, THP:tetrahydro-2H-pyran-2-yl DMSO-$d_6$: deuterated dimethyl sulfoxide

EXAMPLE 1

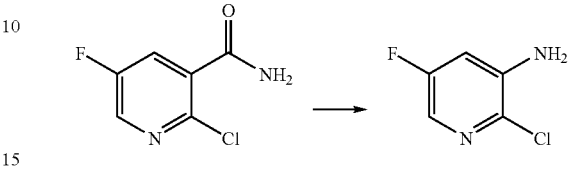

To a solution of 0.11 kg of sodium hydroxide in 1000 mL of water, 1.4 kg of a 12% sodium hypochlorite aqueous solution and 0.40 kg of 2-chloro-5-fluoronicotinamide were added, and the mixture was stirred for 2 hours and 30 minutes at room temperature. The reaction mixture was heated to 45° C. and stirred for 4 hours. The reaction mixture was cooled to room temperature, ethyl acetate and 6 mol/L hydrochloric acid were added thereto. The organic layer was separated and the aqueous layer was extracted with ethyl acetate. The organic layer and the extract were combined, anhydrous magnesium sulfate and activated carbon were added thereto, and the mixture was stirred for 30 minutes at room temperature. Insoluble matter was filtered out and the solvent was evaporated under reduced pressure to give 0.29 kg of 2-chloro-5-fluoropyridin-3-amine as a brown solid.

$^1$H-NMR (CDCl$_3$) δ value: 4.22 (2H, s), 6.79 (1H, dd, J=9.3, 2.7 Hz), 7.67 (1H, d, J=2.7 Hz)

EXAMPLE 2

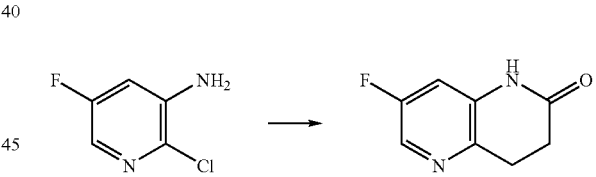

To a suspension of 25.0 g of 2-chloro-5-fluoropyridin-3-amine, 3.8 g of bis(tricyclohexyl phosphine)palladium (II) chloride and 1.5 g of 2-(di-tert-butylphosphino)biphenyl in 75 mL of butyl acrylate, 44.1 g of diisopropylethylamine was added, 15.7 g of formic acid was added dropwise thereto at room temperature, and the mixture was refluxed for 3 hours. To the reaction mixture, 32.1 g of diisopropylethylamine and 11.5 g of formic acid were added at 100° C., and the mixture was refluxed for 5 hours. The reaction mixture was cooled to 80° C., 50 mL of toluene and 75 mL of water were added thereto and the resultant mixture was cooled to room temperature. The solid product was obtained by filtration, and washed using in the order of toluene and water to give 18.0 g of 7-fluoro-3,4-dihydro-1,5-naphthyridin-2(1H)-one as a white solid.

$^1$H-NMR (DMSO-$d_6$) δ value:

2.60 (2H, t, J=7.7 Hz), 3.00 (2H, t, J=7.7 Hz), 7.03 (1H, dd, J=9.8, 2.7 Hz), 8.07 (1H, d, J=2.7 Hz), 10.3 (1H, br s)

EXAMPLE 3

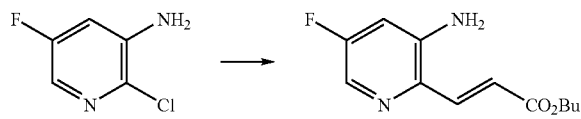

A mixed solution of 150 mL of butyl acetate and 73 mL of butyl acrylate was refluxed with heating for 45 minutes under a nitrogen atmosphere. The reaction mixture was cooled to 30° C., 50.0 g of 2-chloro-5-fluoropyridine-3-amine, 3.8 g of palladium (II) acetate, 44.8 g of triphenylphosphine and 36.6 g of sodium carbonate were added thereto, and the mixture was refluxed for 13 hours under a nitrogen atmosphere. The reaction mixture was cooled to room temperature, 150 mL of water and 700 mL of butyl acetate were added thereto, and the mixture was stirred for 1 hour. Insoluble matter was filtered out, and the filter residue was washed using 50 mL of butyl acetate. The filtrate and the wash liquid were combined, the organic layer was separated, and 800 mL of the solvent was evaporated under reduced pressure. To the obtained residue, 300 mL of cyclohexane and 30 mL of toluene were added dropwise, the mixture was cooled to 5° C., and the solid product was obtained by filtration and washed using a mixed solution of toluene-cyclohexane (1:2) and toluene to give 57.8 g of butyl (2E)-3-(3-amino-5-fluoropyridin-2-yl)acrylate as a yellow solid.

$^1$H-NMR(CDCl$_3$) δ value: 0.96 (3H, t, J=7.3 Hz), 1.38-1.48 (2H, m), 1.64-1.72 (2H, m), 4.10 (2H, brs), 4.21 (2H, t, J=6.6 Hz), 6.72 (1H, dd, J=9.8, 2.3 Hz), 6.86 (1H, d, J=15.1 Hz), 7.7 1 (1H, d, J=15.1 Hz), 7.94 (1H, d, J=2.3 Hz)

EXAMPLE 4

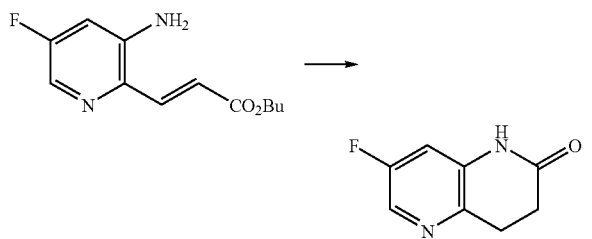

To a suspension of 9.1 g of butyl (2E)-3-(3-amino-5-fluoropyridin-2-yl)acrylate and 0.9 g of 10% palladium carbon in 30 mL of methanol, 4 mL of formic acid was added, and 15 mL of triethylamine was added dropwise thereto under ice cooling. The reaction mixture was stirred at 60° C. for 2 hours. The reaction mixture was cooled to room temperature, insoluble matter was filtered out, and the filter residue was washed using 30 mL of toluene. The filtrate and the wash liquid were combined and the solvent was evaporated under reduced pressure. To the obtained residue, 30 mL of toluene was added, the mixture was stirred at 100° C. for 2 hours and 30 minutes. To the reaction mixture, 30 mL of water was added dropwise at 45° C. and the mixture was cooled to 5° C. The solid product was obtained by filtration and washed in the order of water and toluene to give 5.7 g of 7-fluoro-3,4-dihydro-1,5-naphthyridin-2(1H)-one as a white solid.

$^1$H-NMR (DMSO-d$_6$) δ value:
2.60 (2H, t, J=7.7 Hz), 3.00 (2H, t, J=7.7 Hz), 7.03 (1H, dd, J=9.9, 2.6 Hz), 8.07 (1H, d, J=2.6 Hz), 10.3 (1H, br s)

EXAMPLE 5

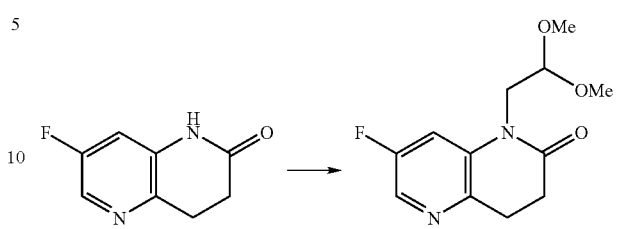

To a suspension of 49.8 g of potassium phosphate in 90 mL dimethyl sulfoxide, 30.0 g of 7-fluoro-3,4-dihydro-1,5-naphthyridin-2(1H)-one and 39.7 g of 2-bromo-1,1-dimethoxyethane were added, and the mixture was stirred at 100° C. for 3 hours. To the mixture, 7.7 g of potassium phosphate and 6.1 g of 2-bromo-1,1-dimethoxyethane were added, and the mixture was stirred for 1 hour at the same temperature. The reaction mixture was cooled to room temperature, and 120 mL of water and 120 mL of toluene were added thereto. The mixture was adjusted to pH 8.5 with acetic acid, and 3.0 g of activated carbon was added thereto. Insoluble matter was filtered out, and the filter residue was washed using 30 mL of toluene and 30 mL of water. The filtrate and the wash liquid were combined, the organic layer was separated, and the aqueous layer was extracted with 60 mL of toluene. The organic layer and the extract were combined to evaporate the solvent under reduced pressure, 90 mL of dibutyl ether was added thereto, and the mixture was cooled to −3° C. The solid product was obtained by filtration and washed using in the order of dibutyl ether and water to give 30.8 g of 1-(2,2-dimethoxyethyl)-7-fluoro-3,4-dihydro-1,5-naphthyridin-2 (1H)-one as a light yellow solid.

$^1$H-NMR (CDCl$_3$) δ value: 2.73-2.83 (2H, m), 3.07-3.14 (2H, m), 3.44 (6H, s), 3.93 (2H, d, J=5.4 Hz), 4.61 (1H, t, J=5.4 Hz), 7.45 (1H, dd, J=10.5, 2.4 Hz), 8.06 (1H, d, J=2.4 Hz)

EXAMPLE 6

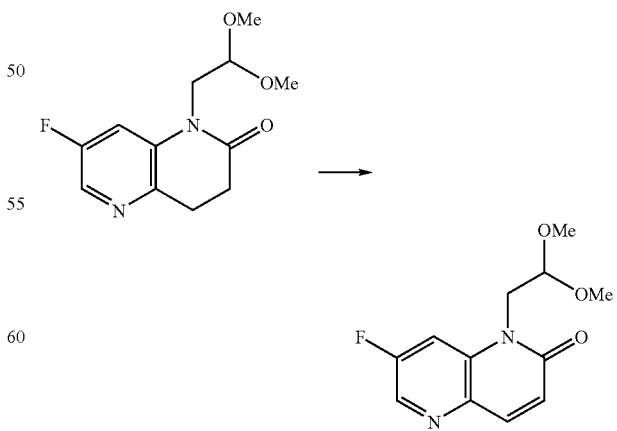

To a suspension of 5.0 g of 1-(2,2-dimethoxyethyl)-7-fluoro-3,4-dihydro-1,5-naphthyridin-2(1H)-one, 5.3 g of N-bromosuccinimide and 3.0 g of potassium carbonate in 30 mL of chlorobenzene, 0.12 g of 2,2'-azobis(4-methoxy-2,4-dimethylvaleronitrile) was added three times hourly at 50 to 60° C. under a nitrogen atmosphere. After stirring the reaction mixture for 1 hour at the same temperature, 10 mL of water was added thereto, and the mixture was adjusted to pH 12.6 using a 20% sodium hydroxide solution. The organic layer was separated and washed with 15 mL of water. The aqueous layer was extracted with 15 mL of toluene. The organic layer and the extract were combined to evaporate the solvent under reduced pressure. To the obtained residue, 2 mL of chlorobenzene and 6 mL of cyclohexane were added, the mixture was stirred for 30 minutes under ice cooling, and the solid product was obtained by filtration and washed with cyclohexane to give 4.1 g of 1-(2,2-dimethoxyethyl)-7-fluoro-1,5-naphthyridin-2(1H)-one as a light yellow solid.

$^1$H-NMR (CDCl$_3$) δ value:
3.44 (6H, s), 4.30 (2H, d, J=5.3 Hz), 4.65 (1H, t, J=5.3 Hz), 6.87 (1H, d, J=9.8 Hz), 7.71 (dd, 1H, J=10.6, 2.4H z), 7.92 (1H, d, J=9.8 Hz), 8.41 (1H, d, J=2.4 Hz)

EXAMPLE 7

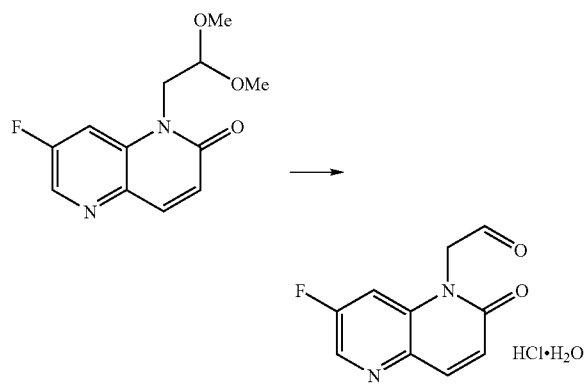

To a suspension of 158 g of 1-(2,2-dimethoxyethyl)-7-fluoro-1,5-naphthyridin-2(1H)-one in 1.26 L of 2-butanone, 79 mL of 12 mol/L hydrochloric acid was added at room temperature, and the mixture was refluxed for 3 hours. After cooling the reaction mixture to 10° C., the solid product was obtained by filtration and washed with 2-butanone to give 152 g of (7-fluoro-2-oxo-1,5-naphthyridin-1(2H)-yl)acetaldehyde hydrochloride monohydrate as a light yellow solid.

$^1$H-NMR (DMSO-d$_6$) δ value: 5.27 (2H, s), 6.88 (1H, d, J=9.9 Hz), 7.99-8.04 (2H, m), 8.58 (1H, d, J=2.4 Hz), 9.68 (1H, s)

EXAMPLE 8

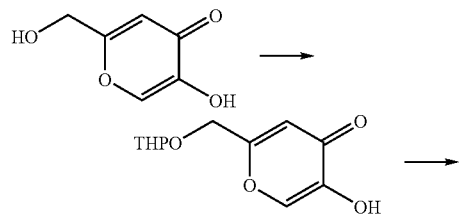

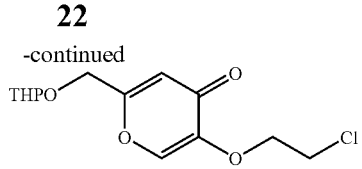

To a suspension of 14.3 g of kojic acid in 57 mL of tetrahydrofuran, 11 mL of 3,4-dihydro-2H-pyran and 77 mg of p-toluenesulfonic acid monohydrate were added, and the mixture was stirred for 6 hours at room temperature. To the mixture, 1 mL of a 0.5 mol/L sodium hydroxide aqueous solution was added, and the solvent was evaporated under reduced pressure to give 26.8 g of 5-hydroxy-2-((tetrahydro-2H-pyran-2-yloxy)methyl)-4H-pyran-4-one as a light yellow solid.

To a solution of the obtained 5-hydroxy-2-(tetrahydro-2H-pyran-2-yloxy)methyl)-4H-pyran-4-one in 45 mL of N,N-dimethylformamide, 45 mL of toluene, 20.8 mL of 1-bromo-2-chloroethane and 41.6 g of potassium carbonate were added, and the mixture was stirred for 4 hours at 60° C. The mixture was allowed to stand overnight at room temperature, and the solvent was evaporated under reduced pressure. To the obtained residue, 107 mL of water and 90 mL of ethyl acetate-17 mL of toluene were added. The organic layer was separated, and the aqueous layer was extracted using 90 mL of ethyl acetate-17 mL of toluene. The organic layer and the extract were combined and the solvent was evaporated under reduced pressure to give 26.7 g of 5-(2-chloroethoxy)-2-((tetrahydro-2H-pyran-2-yloxy)methyl)-4H-pyran-4-one as a brown oily substance.

$^1$H-NMR (DMSO-d$_6$) δ value: 1.52-1.71 (4H, m), 1.73-1.79 (1H, m), 1.80-1.88 (1H, m), 3.56 (1H, dddd, J=11.1, 4.4, 4.2, 1.4 Hz), 3.79 (2H, t, J=6.0 Hz), 3.80-3.85 (1H, m), 4.27 (2H, t, J=6.0 Hz), 4.31-4.37 (1H, m), 4.49-4.55 (1H, m), 4.73 (1H, t, J=3.4 Hz), 6.52 (1H, s), 7.75 (1H, s)

EXAMPLE 9

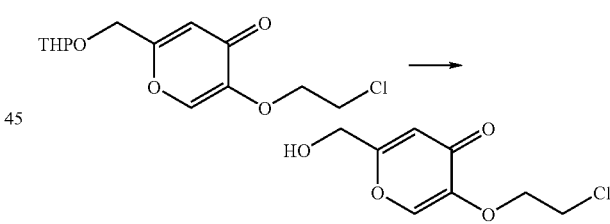

To a solution of 314 g of 5-(2-chloroethoxy)-2-((tetrahydro-2H-pyran-2-yloxy)methyl)-4H-pyran-4-one in 630 mL of methanol, 6.3 mL of concentrated hydrochloric acid was added and the mixture was stirred for 6 hours at room temperature. To the reaction mixture, 13 mL of 28% ammonia water was added and the solvent was evaporated under reduced pressure to give 240 g of 5-(2-chloroethoxy)-2-(hydroxymethyl)-4H-pyran-4-one (crude product) as a brown oily substance.

10.6 g of the obtained oily substance was purified by silica gel column chromatography [silica gel; KANTO CHEMICAL CO., INC., silica gel 60, eluate; chloroform:methanol=95:5] to give 7.0 g of 5-(2-chloroethoxy)-2-(hydroxymethyl)-4H-pyran-4-one as a light brown solid.

$^1$H-NMR (CDCl$_3$) δ value:
3.05 (1H, s), 3.79 (2H, t, J=5.9 Hz), 4.25 (2H, t, J=59 Hz), 4.50 (2H, s), 6.53 (1H, t, J=0.9 Hz), 7.75 (1H, s)

EXAMPLE 10

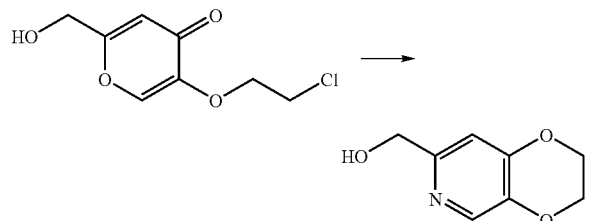

To 229 g of 5-(2-chloroethoxy)-2-(hydroxymethyl)-4H-pyran-4-one (crude product), 572 mL of 28% ammonia water was added, the mixture was stirred for 7 hours at 85° C. and allowed to stand overnight at room temperature. The reaction mixture was extracted 4 times with 500 mL of 2-propyl acetate. The organic layer was combined therewith and the solvent was evaporated under reduced pressure to give 90.5 g of (2,3-dihydro-(1,4)dioxino(2,3-c)pyridin-7-yl)methanol as a brown oily substance.

$^1$H-NMR (CDCl$_3$) δ value: 4.25-4.38 (4H, m), 4.62 (2H, s), 6.76 (1H, s), 8.11 (1H, s)

EXAMPLE 11

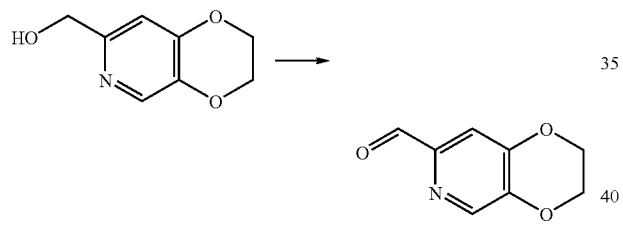

To a solution of 111 g of (2,3-dihydro-(1,4)dioxino(2,3-c)pyridin-7-yl)methanol in 1110 mL of tetrahydrofuran, 164 g of manganese dioxide was added, the mixture was stirred for 5 hours at 70° C. and stirred overnight at room temperature. The reaction mixture was subjected to celite filtration and the filter residue was washed with 500 mL of tetrahydrofuran. The filtrate and the wash liquid were combined to evaporate the solvent under reduced pressure. The obtained residue was recrystallized from 750 mL of 2-propanol to give 53.5 g of 2,3-dihydro-(1,4)dioxino(2,3-c)pyridin-7-carbaldehyde as a light yellow solid.

$^1$H-NMR (CDCl$_3$) δ value: 4.38 (4H, s), 7.51 (1H, s), 8.31 (1H, s), 9.92 (1H, s)

EXAMPLE 12

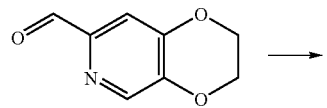

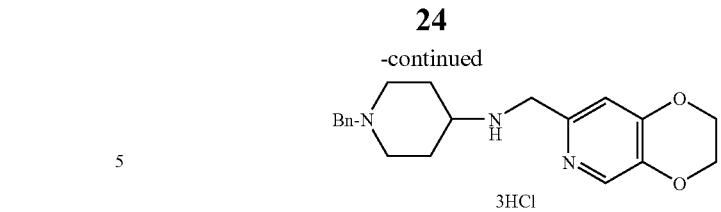

A solution of 3.0 g of 2,3-dihydro-(1,4)dioxino(2,3-c)pyridin-7-carbaldehyde and 3.4 g of 4-amino-1-benzylpiperidine in 30 mL of methanol was stirred for 50 minutes at room temperature, and a solution of 0.34 g of sodium borohydride in 30 mL of 0.01 mol/L sodium hydroxide/methanol was added dropwise thereto under ice cooling. The mixture was further stirred for 2 hours under ice cooling, 6 mL of concentrated hydrochloric acid was added dropwise thereto at 10° C. or lower and stirred for 1 hour 30 minutes. The solid product was obtained by filtration to give 6.8 g of 1-benzyl-N-(2,3-dihydro-(1,4)dioxino(2,3-c)pyridin-7-ylmethyl)piperidin-4-amine trihydrochloride as a white solid.

$^1$H-NMR (D$_2$O) δ value: 1.93-2.03 (2H, m), 2.48 (2H, d, J=13.3 Hz), 3.13-3.21 (2H, m), 3.62-3.73 (3H, m), 4.37 (2H, s), 4.43-4.49 (4H, m), 4.53-4.58 (2H, m), 7.35 (1H, s), 7.49-7.57 (5H, m), 8.30 (1H, s)

EXAMPLE 13

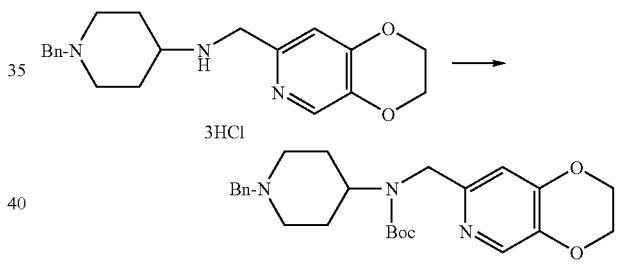

To a solution of 6.8 g of 1-benzyl-N-(2,3-dihydro-(1,4)dioxino(2,3-c)pyridin-7-ylmethyl)piperidin-4-amine trihydrochloride in 20 mL of water-11 mL of tetrahydrofuran, 8 mL of a 20% sodium hydroxide aqueous solution was added under ice cooling, and subsequently 3.3 g of di-tert-butyl dicarbonate was added thereto. The mixture was stirred for 8 hours at room temperature and 11 mL of ethyl acetate was added thereto. The organic layer was separated and 5.1 g of silica gel (Chromatorex-NH, FUJI SILYSIA CHAMICAL LTD.) was added thereto. The mixture was stirred for 1 hour at room temperature and filtrated by passing through 2.6 g of silica gel (Silica gel 60N, KANTO CHEMICAL CO., INC). For washing, 35 mL of ethyl acetate was used. The filtrate and the wash liquid were combined and the solvent was evaporated under reduced pressure to give 6.3 g of tert-butyl (1-benzylpiperidin-4-yl)(2,3-dihydro-(1,4)dioxino(2,3-c)pyridin-7-ylmethyl)carbamate as a light yellow foam.

$^1$H-NMR (CDCl$_3$) δ value: 1.32-1.54 (9H, m), 1.55-1.74 (4H, m), 1.92-2.07 (2H, m), 2.87 (2H, d, J=11.5 Hz), 3.44 (2H, s), 4.07-4.18 (1H, m), 4.22-4.32 (4H, m), 4.33-4.48 (2H, m), 6.72 (1H, s), 7.20-7.24 (1H, m), 7.27-7.31 (4H, m), 8.04 (1H, s)

EXAMPLE 14

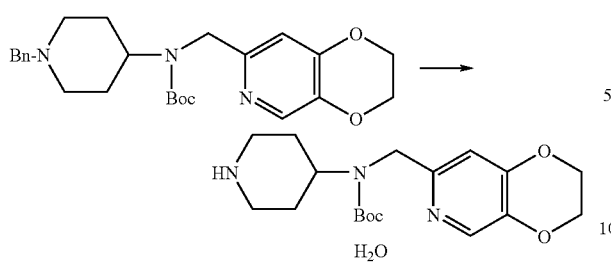

To a solution of 5.9 g of tert-butyl (1-benzylpiperidin-4-yl)(2,3-dihydro-(1,4)dioxino(2,3-c)pyridin-7-yl methyl)carbamate in 30 mL of methanol, 1.2 g of 5% palladium carbon was added, and the mixture was stirred for 7 hours at 60° C. under a hydrogen atmosphere. The mixture was subjected to celite filtration, and 40 mL of ethyl acetate and 30 mL of a 0.5 mol/L sodium hydroxide aqueous solution were added to the filtrate. The organic layer was washed with saturated sodium chloride solution, dried using sodium sulfate and the solvent was evaporated under reduced pressure. The obtained residue was recrystallized from 5 mL of ethyl acetate-15 mL of heptane to give 3.0 g of tert-butyl ((2,3-dihydro-(1,4)dioxino(2,3-c)pyridin-7-yl)methyl)(piperidin-4-yl)carbamate monohydrate as a white powder.

$^1$H-NMR(CDCl$_3$) δ value: 1.39 (9H, s), 1.48-1.53 (2H, m), 1.63-1.68 (2H, m), 2.61-2.66 (2H, m), 3.07-3.10 (2H, m), 4.26-4.38 (7H, m), 6.75 (1H, s), 8.05 (1H, s)

EXAMPLE 15

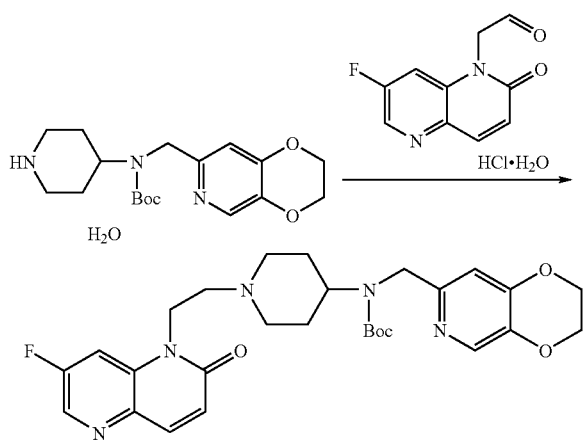

To a solution of 5.0 g of tert-butyl (2,3-dihydro(1,4)dioxino(2,3-c)pyridin-7-ylmethyl)(piperidin-4-yl)carbamate monohydrate in 40 mL of N-methyl-2-pyrrolidone, 3.5 g of (7-fluoro-2-oxo-1,5-naphthyridin-1(2H)-yl)acetaldehyde hydrochloride monohydrate was added, and the mixture was stirred for 1 hour at room temperature. To the mixture, 4.3 g of sodium triacetoxyborohydride was added dividedly in 5 portions over the period of 80 minutes under ice cooling, and the mixture was stirred for 1 hour and 40 minutes under ice cooling. After heating to room temperature, the mixture was added with 20 mL of water and adjusted to pH 11.5 with an aqueous solution of 20% sodium hydroxide. To the mixture, 20 mL of N-methyl-2-pyrrolidone was added at 70 to 80° C., and the mixture was stirred for 2 hours and 30 minutes at the same temperature. The reaction mixture was cooled to room temperature and the solid product was obtained by filtration and washed with water to give 6.5 g of tert-butyl (2,3-dihydro(1,4)dioxino(2,3-c)pyridin-7-ylmethyl)(1-(2-(7-fluoro-2-oxo-1,5-naphthyridin-1(2H)-yl)ethyl)piperidin-4-yl)carbamate as a light brown solid.

$^1$H-NMR (CDCl$_3$) δ value: 1.30-1.80 (13H, m), 2.08-2.27 (2H, m), 2.56-2.65 (2H, m), 2.93-3.04 (2H, m), 4.02-4.19 (1H, m), 4.23-4.49 (8H, m), 6.73 (1H, s), 6.84 (1H, d, J=9.9 Hz), 7.47 (1H, dd, J=10.2, 2.3 Hz), 7.87 (1H, d, J=9.9 Hz), 8.05 (1H, s), 8.41 (1H, d, J=2.3 Hz)

EXAMPLE 16

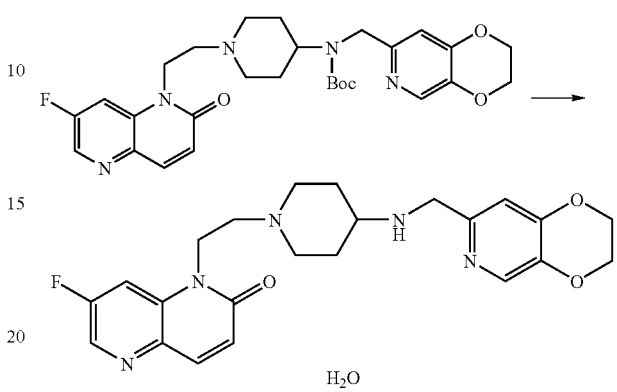

To a suspension of 25.0 g of tert-butyl (2,3-dihydro(1,4)dioxino(2,3-c)pyridin-7-ylmethyl)(1-(2-(7-fluoro-2-oxo-1,5-naphthyridin-1(2H)-yl)ethyl)piperidin-4-yl)carbamate in 50 mL of water, 18 mL of concentrated hydrochloric acid was added dropwise at 28 to 39° C. The reaction mixture was stirred for 3 hours and 30 minutes at 40 to 50° C., cooled to room temperature, added with 17 mL of a 20% sodium hydroxide aqueous solution and 25 mL of water and heated to 60° C. The mixture was adjusted to pH 3 with concentrated hydrochloric acid and 25 mL of water was added thereto. Insoluble matter was filtered out at 50° C. and the filter residue was washed using 25 mL of water. The filtrate and the wash liquid were combined and heated to 40° C., added with 13.5 mL of a 20% sodium hydroxide aqueous solution, 150 mL of 2-butanone and 25 mL of water, and refluxed with heating to dissolve the solid matter. The reaction mixture was cooled to 10° C. and the solid product obtained by filtration was washed with water to give 19.3 g of 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrate as a light yellow solid.

$^1$H-NMR (CDCl$_3$) δ value: 1.35-1.50 (2H, m), 1.90 (2H, d, J=12.2 Hz), 2.18 (2H, td, J=11.5, 2.2 Hz), 2.46-2.59 (1H, m), 2.64 (2H, t, J=7.1 Hz), 2.95 (2H, d, J=12.0 Hz), 3.79 (2H, s), 4.26-4.34 (6H, m), 6.81 (1H, s), 6.85 (1H, d, J=9.8 Hz), 7.56 (1H, dd, J=10.2, 2.4 Hz), 7.88 (1H, dd, J=9.8, 0.5 Hz), 8.10 (1H, s), 8.41 (1H, d, J=2.4 Hz)

EXAMPLE 17

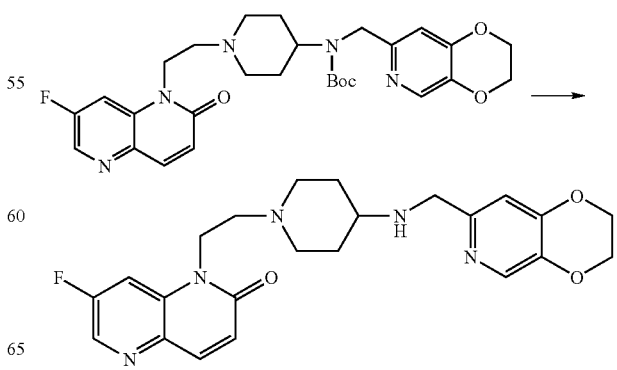

A solution of 3.03 g of tert-butyl (2,3-dihydro(1,4)dioxino (2,3-c)pyridin-7-ylmethyl)(1-(2-(7-fluoro-2-oxo-1,5-naphthyridin-1(2H)-yl)ethyl)piperidin-4-yl)carbamate in 45 mL of trifluoroacetic acid was stirred for 1 hour and 30 minutes at room temperature. The reaction mixture was cooled with ice, added with 30 mL of water and 30 mL of ethyl acetate, and adjusted to pH 10 with a 2 mol/L sodium hydroxide aqueous solution. The organic layer was separated and the aqueous layer was extracted 7 times with ethyl acetate. The organic layer was combined therewith and the solvent was concentrated to 10 mL under reduced pressure, whereby insoluble matter was filtered out. The solvent was evaporated under reduced pressure, and the obtained residue was purified by basic silica gel column chromatography [eluate; chloroform:methanol=92:8], recrystallized from 3 mL of ethyl acetate to give 0.611 g of 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one (anhydrate) as a light yellow solid.

$^1$H-NMR(CDCl$_3$) δ value: 1.39-1.47 (2H, m), 1.87-1.93 (2H, m), 2.18 (2H, t, J=10.8 Hz), 2.49-2.55 (1H, m), 2.64 (2H, t, J=7.1 Hz), 2.92-2.98 (2H, m), 3.79 (2H, s), 4.26-4.29 (2H, m), 4.29-4.34 (4H, m), 6.82 (1H, s), 6.85 (1H, d, J=9.6 Hz), 7.55 (1H, d, J=9.6 Hz), 7.88 (1H, d, J=9.6 Hz), 8.10 (1H, s), 8.41 (1H, d, J=2.3 Hz)

Anal. Calcd. For C23H26FN5O3: C, 62.86; H, 5.96; H, 15.94; N, 15.94; F, 4.32

Found: C, 62.58; H, 5.92; N, 15.80; F, 4.21

COMPARATIVE EXAMPLE 1

WO 2007/138974

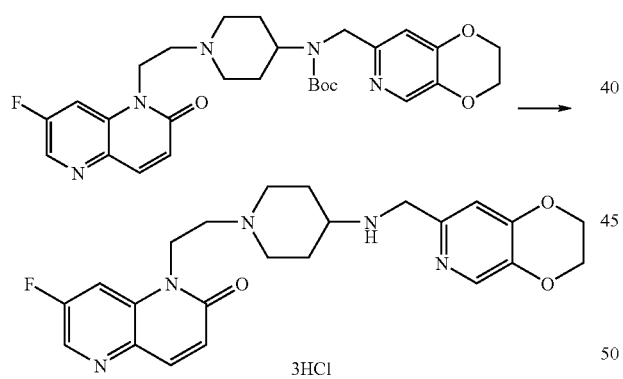

To a suspension of 0.30 g of tert-butyl (2,3-dihydro(1,4)dioxino(2,3-c)pyridin-7-ylmethyl)(1-(2-(7-fluoro-2-oxo-1,5-naphthyridin-1(2H)-yl)ethyl)piperidin-4-yl)carbamate in 2 mL of 2-propanol, 0.23 mL of concentrated hydrochloric acid was added, and the resultant mixture was stirred for 1 hour and 50 minutes under reflux with heating. The reaction mixture was cooled to 5° C., and the solid was obtained by filtration to give 0.28 g of 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one trihydrochloride as a light yellow solid.

$^1$H-NMR (D$_2$O) δ value: 2.00-2.16 (2H, m), 2.52-2.61 (2H, m), 3.23-3.35 (2H, m), 3.61-3.67 (2H, m), 3.69-3.80 (1H, m), 3.98-4.07 (2H, m), 4.46-4.51 (2H, m), 4.52 (2H, s), 4.55-4.63 (2H, m), 4.71-4.96 (2H, m), 6.99 (1H, d, J=9.8 Hz), 7.44 (1H, s), 7.93-7.99 (1H, m), 8.10 (1H, d, J=9.8 Hz), 8.36 (1H, s), 8.57 (1H, d, J=2.2 Hz)

PRODUCTION EXAMPLE 1

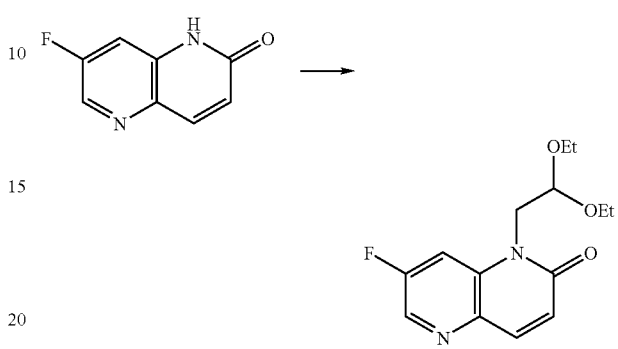

To a suspension of 3.00 g of 7-fluoro-1,5-naphthyridin-2(1H)-one and 5.04 g of potassium phosphate in 12 mL of dimethyl sulfoxide, 4.68 g of 2-bromo-1,1-diethoxyethane was added at room temperature, and the resultant mixture was stirred for 4.5 hours at 94° C. The reaction mixture was cooled, and 21 mL of water and 12 mL of cyclopentyl methyl ether were added thereto. The mixture was adjusted to pH 5.8 with 12 mol/L hydrochloric acid, subsequently the insoluble matter was filtered out, and the filter residue was washed twice with 3 mL of cyclopentyl methyl ether. The organic layers of the obtained filtrate and the wash liquid were separated, and the solvent was evaporated under reduced pressure. The obtained residue was purified by silica gel column chromatography to give 3.11 g of 1-(2,2-diethoxyethyl)-7-fluoro-1,5-naphthyridin-2(1H)-one as a light yellow oily substance.

$^1$H-NMR (CDCl$_3$) δ value: 1.12 (6H, t, J=7.1 Hz), 3.47-3.55 (2H, m), 3.74-3.82 (2H, m), 4.29 (2H, d, J=5.1 Hz), 4.78 (1H, t, J=5.4 Hz), 6.86 (1H, d, J=9.8 Hz), 7.82 (1H, dd, J=10.6, 2.4 Hz), 7.92 (1H, d, J=9.8 Hz), 8.41 (1H, d, J=2.4 Hz)

PRODUCTION EXAMPLE 2

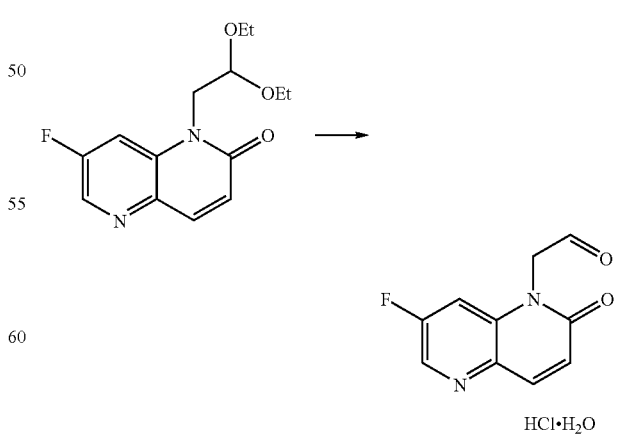

To 480 mL of 2-butanone, 30 mL of 12 mol/L hydrochloric acid was added, the mixture was heated to 70° C. and a solution of 60 g of 1-(2,2-diethoxyethyl)-7-fluoro-1,5-naphthyridin-2(1H)-one in 60 mL of 2-butanone was added dropwise, followed by reflux for 2 hours. After cooling the reaction mixture to 25° C., the solid product was obtained by filtration and washed with 2-butanone to give 50.3 g of (7-fluoro-2-oxo-1,5-naphthyridin-1(2H)-yl)acetaldehyde hydrochloride monohydrate as a light yellow solid.

BRIEF DESCRIPTION OF THE DRAWINGS

FIG. 1 shows the powder X-ray diffraction pattern of 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrate.

INDUSTRIAL APPLICABILITY

The 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrate of the present invention (1) has strong antibacterial activity and high safety, (2) does not exhibit deliquescence or hygroscopicity, (3) is easy to handle, (4) is produced using a solvent which is safe to human body, (5) is produced under conditions with a little environmental burden, and (6) can be mass produced, thereby being useful as a bulk pharmaceutical.

The invention claimed is:

1. Crystals of 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrate.

2. An antibacterial agent containing crystals of 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrate.

3. A composition, comprising crystals of 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one monohydrate of claim 1, and at least one of excipient, a carrier and a diluent.

* * * * *